(12) United States Patent
Govari et al.

(10) Patent No.: US 11,179,203 B2
(45) Date of Patent: Nov. 23, 2021

(54) POSITION-TRACKING-ENABLING CONNECTOR FOR AN EAR-NOSE-THROAT (ENT) TOOL

(71) Applicant: Biosense Webster (Israel) Ltd., Yokneam (IL)

(72) Inventors: Assaf Govari, Haifa (IL); Vadim Gliner, Haifa (IL); Alon Boumendil, Givat Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 771 days.

(21) Appl. No.: 15/795,169

(22) Filed: Oct. 26, 2017

(65) Prior Publication Data
US 2019/0125450 A1    May 2, 2019

(51) Int. Cl.
| | | |
|---|---|---|
| *A61B 34/20* | (2016.01) | |
| *A61B 17/24* | (2006.01) | |
| *A61B 90/98* | (2016.01) | |
| *A61B 5/06* | (2006.01) | |
| *G06F 21/10* | (2013.01) | |

(Continued)

(52) U.S. Cl.
CPC .............. *A61B 34/20* (2016.02); *A61B 5/062* (2013.01); *A61B 17/24* (2013.01); *A61B 90/98* (2016.02); *G06F 21/10* (2013.01); *A61B 5/065* (2013.01); *A61B 2017/00199* (2013.01); *A61B 2017/00482* (2013.01); *A61B 2034/2051* (2016.02); *A61B 2034/2059* (2016.02); *A61B 2090/0803* (2016.02); *A61B 2090/0814* (2016.02); *A61B 2560/028* (2013.01); *A61B 2562/08* (2013.01);

(Continued)

(58) Field of Classification Search
CPC .......... A61B 17/24; A61B 2017/00199; A61B 2017/00482; A61B 2034/2051; A61B 2034/2059; A61B 2090/0803; A61B 2090/0814; A61B 2562/08; A61B 2562/227; A61B 34/20; A61B 5/062; A61B 5/065; A61B 90/98; G06F 21/10; H04B 5/0062
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |

(Continued)

FOREIGN PATENT DOCUMENTS

| | | |
|---|---|---|
| EP | 3381384 | 10/2018 |
| WO | WO 96/05768 A1 | 2/1996 |
| WO | WO 2017/074977 | 5/2017 |

OTHER PUBLICATIONS

European Search Report dated Mar. 22, 2019 from corresponding European Patent Application No. 18202555.1.

*Primary Examiner* — Amelie R Davis
(74) *Attorney, Agent, or Firm* — Frost Brown Todd LLC

(57) ABSTRACT

A medical instrument includes a shaft, one or more position sensors, a connector and interrogation circuitry. The shaft is configured for insertion into a body of a patient. The one or more position sensors are fitted at a distal end of the shaft. The connector is configured to receive a mating connector. The interrogation circuitry is configured to detect whether the mating connector is connected to the connector, and, if not connected, to prevent tracking a position of the distal end in the body using the one or more position sensors.

10 Claims, 3 Drawing Sheets

(51) Int. Cl.
*A61B 90/00* (2016.01)
*A61B 17/00* (2006.01)
*H04B 5/00* (2006.01)

(52) U.S. Cl.
CPC ...... *A61B 2562/227* (2013.01); *H04B 5/0062* (2013.01)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,796,040 B2 | 9/2010 | Mezhinsky et al. |
| 7,840,254 B2 | 11/2010 | Glossop |
| 8,035,487 B2 | 10/2011 | Malackowski |
| 8,190,389 B2 | 5/2012 | Kim et al. |
| 8,535,342 B2 | 9/2013 | Malackowski et al. |
| 8,821,376 B2 | 9/2014 | Tolkowsky |
| 8,942,780 B2 | 1/2015 | Scully et al. |
| 8,961,398 B2 | 2/2015 | Makower et al. |
| 9,167,961 B2 | 10/2015 | Makower et al. |
| 2002/0032380 A1* | 3/2002 | Acker ............... A61B 1/00062 600/439 |
| 2002/0065455 A1 | 5/2002 | Ben-Haim et al. |
| 2002/0161421 A1* | 10/2002 | Lee ..................... G01R 33/285 607/116 |
| 2003/0120150 A1 | 6/2003 | Govari |
| 2004/0068178 A1 | 4/2004 | Govari |
| 2007/0225550 A1 | 9/2007 | Gattani et al. |
| 2010/0261967 A1 | 10/2010 | Pacey et al. |
| 2011/0238063 A1* | 9/2011 | Gregg ................ A61B 18/1233 606/41 |
| 2014/0066944 A1 | 3/2014 | Taylor et al. |
| 2014/0275765 A1* | 9/2014 | Gebhart ................. G01J 3/453 600/103 |
| 2014/0275997 A1 | 9/2014 | Chopra et al. |
| 2015/0155912 A1* | 6/2015 | Winward ............ A61B 5/0215 375/257 |
| 2016/0066770 A1 | 3/2016 | Barbato et al. |
| 2017/0119473 A1* | 5/2017 | Clopp ................... A61M 25/09 |
| 2017/0143366 A1* | 5/2017 | Groene ......... A61B 17/320092 |
| 2018/0085036 A1* | 3/2018 | Bocquet ................ A61B 90/98 |

* cited by examiner

POSITION-TRACKING-ENABLING CONNECTOR FOR AN EAR-NOSE-THROAT (ENT) TOOL

FIELD OF THE INVENTION

The present invention relates generally to methods and devices related to invasive medical instruments, and particularly to methods and devices for enabling position tracking capabilities with invasive medical instruments.

BACKGROUND OF THE INVENTION

Certain invasive procedures require the tracking of a position of a distal end of a medical instrument in the body. For example, U.S. Pat. No. 8,961,398 describes methods and apparatus for treating disorders of the ear, nose, throat or paranasal sinuses. Embodiments include navigation devices for use in conjunction with image guidance or navigation system and hand-held devices having an identification module. The identification module enables a navigational localizer to identify the type of a navigational adaptor that is being connected to navigational localizer. This enables the registration of the location and orientation of the distal tip of navigational adaptor.

As another example, U.S. Patent Application Publication 2014/0066944, issued as U.S. Pat. No. 9,554,864 on Jan. 31, 2007, describes a system and method for tool exchange during surgery for cooperatively controlled robots. The system comprises a tool-holder for receiving a surgical tool adapted to be held by a robot and a surgeon. The system comprises a sensor for detecting if the surgical tool is docked within the tool-holder, and a selector for automatically selecting different movements or actions of the tool-holder to be performed based upon information detected by the sensor.

U.S. Pat. No. 7,796,040 describes a smart connector system that includes a machine connector disposed on a face of a surgical machine, an RFID reader antenna located in close proximity to the machine connector and the face of the surgical machine, and an accessory connector adapted to couple with the machine connector. The accessory connector has an RFID tag antenna and is capable of attaching a tool to the surgical machine. When the accessory connector is brought within close proximity to the machine connector, a communications connection is established between the RFID tag antenna and the RFID reader antenna.

U.S. Pat. No. 8,035,487 describes a surgical tool system comprising a control console, a powered surgical device, an intermediate attachment removably connected to the surgical device and a cutting accessory removably connected to the intermediate attachment. Internal to the cutting accessory is an identification device that contains data specific to the operation of the accessory. The control console, through the transfer of signals through the powered surgical device and the intermediate attachment reads the data in the cutting accessory. Based on these data, the control console selectively actuates the powered surgical device. In some versions of the invention, the identification device may be an RFID chip. The identification device internal to the intermediate attachment provides the control console with data describing the intermediate attachment.

SUMMARY OF THE INVENTION

An embodiment of the present invention provides a medical instrument including a shaft, one or more position sensors, a connector and interrogation circuitry. The shaft is configured for insertion into a body of a patient. The one or more position sensors are fitted at a distal end of the shaft. The connector is configured to receive a mating connector. The interrogation circuitry is configured to detect whether the mating connector is connected to the connector, and, if not connected, to prevent tracking a position of the distal end in the body using the one or more position sensors.

In some embodiments, the medical instrument further includes a tool that is coupled to the distal end of the shaft and is configured to perform an Ear-Nose-Throat (ENT) procedure.

In some embodiments, the one or more position sensors are configured to send position signals to a position tracking system.

There is additionally provided, in accordance with an embodiment of the present invention, an ENT position-tracking-enabling connector that includes a case, a mating connector on the case and enablement circuitry. The mating connector is configured to connect the ENT position-tracking-enabling connector to a medical instrument. The enablement circuitry, which is contained in the case, is configured, when connected to the medical instrument, to enable tracking a position of a distal end of the medical instrument in a body of a patient.

In some embodiments, the enablement circuitry includes a Radio-Frequency Identification (RFID) circuit that is configured to validate position-tracking terms-of-use, and to enable tracking the position of the distal end only when the terms-of-use are valid.

In some embodiments, the ENT position-tracking-enabling connector further includes a counter circuit, which is encoded with a preset maximal number of usage-sessions of the medical instrument and is configured to indicate to the enablement circuitry whether the preset maximal number of usage-sessions has been reached.

In an embodiment, the enablement circuitry is configured to prevent tracking the position of the distal end, upon receiving from the counter circuit an indication that a preset maximal number of usage-sessions value has been reached.

In another embodiment, the enablement circuitry and the counter circuit are both integrated on a single circuit board.

There is further provided, in accordance with an embodiment of the present invention, a method including, for a medical instrument that includes a shaft for insertion into a body of a patient, one or more position sensors fitted at a distal end of the shaft, and a connector, checking whether a mating connector is connected to the connector. If the mating connector is not connected, tracking a position of the distal end in the body using the one or more position sensors is prevented.

There is also provided, in accordance with an embodiment of the present invention, a position tracking enablement method including, in a position-tracking-enabling device that comprises a case and a connector on the case, checking whether the connector is connected to a mating connector in a medical instrument. When the connector is connected to the medical instrument, tracking of a position of a distal end of the medical instrument in a body of a patient is enabled.

The present invention will be more fully understood from the following detailed description of the embodiments thereof, taken together with the drawings in which:

DETAILED DESCRIPTION OF EMBODIMENTS

Overview

ENT position tracking capabilities allow ENT physicians to successfully navigate flexible invasive medical instruments though complicated structures comprising multiple openings, and narrow and/or winding canals. Nevertheless, in many clinical cases these costly position tracking capabilities are not medically required. Unmanaged provisioning of costly position tracking capabilities may unnecessarily increase the cost of a medical procedure.

Embodiments of the present invention that are described herein below provide a position-tracking-enabling connector that enables the physician to apply position tracking capabilities selectively, e.g., as required medically and/or approved financially. In some embodiments, the ENT medical instrument can be operated with or without position tracking, in flexible modes of operation that allow the physician to manage the incurred costs of the medical procedure.

In some embodiments, an ENT invasive instrument is fitted at its distal end with a position sensor, and is configured to accept an ENT position-tracking-enabling connector in a receptacle fitted at its proximal end. The position sensor is configured to produce position signals that are indicative of a position of the distal end of the ENT invasive instrument in the ENT system of a patient. The position-tracking-enabling connector is configured to enable such capabilities only if terms of use (possibly encoded in the position-tracking-enabling connector) are valid, such as a valid expiration date and/or one or more usage-sessions are available. In an embodiment, the position-tracking-enabling connector alerts the physician when the preset maximal number of usage-sessions has been reached.

The disclosed techniques assist the physician and the healthcare system to control the cost of care, and implement pricy position tracking capabilities only when necessarily, and in a budget-minded manner. Moreover, the disclosed techniques enable the physician to selectively use expensive associated tooling, such as high-end, high-quality, multiple-use insertion tube tools equipped with position sensors, while being able to flexibly plan and manage the costs of equipment and operation.

System Description

Figure 1:
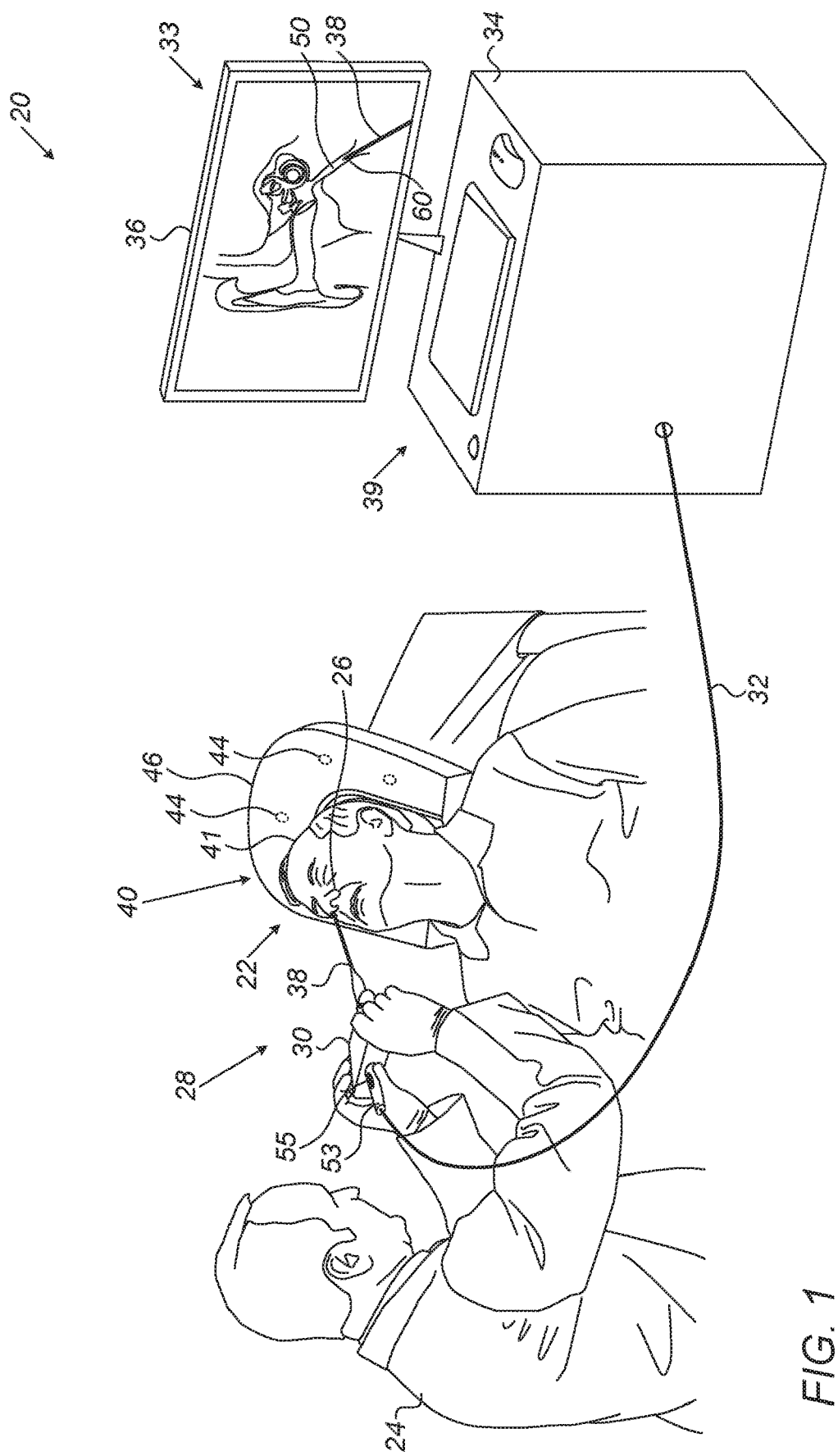
FIG. 1 is a schematic, pictorial illustration of an ENT treatment system comprising a position-tracking-enabling connector, in accordance with an embodiment of the present invention.

FIG. 1 is a schematic, pictorial illustration of an ENT treatment system 20 comprising an ENT position-tracking-enabling connector 55, in accordance with an embodiment of the present invention. In some embodiments, ENT position tracking and treatment system 20 comprises a medical instrument, such an ENT insertion tube 28, which is configured to diagnose and/or treat an ENT medical condition, such as infection in an Eustachian tube 50 of a patient 22.

ENT insertion tube 28 comprises a tool fitted at its distal end, such as an ENT tool 38, which a physician 24 inserts into a nose 26 of patient 22. As seen on display 36, ENT tool 38 comprises a position sensor 60. ENT insertion tube 28 further comprises a handheld ENT apparatus 30, coupled to a proximal end of ENT tool 38 and configured to assist physician 24 in manipulate tool 38 into Eustachian tube 50 through a nose 26 and in applying the treatment. ENT apparatus 30 is configured with a receptacle, which may be located at a handle 53. The receptacle is able to receive ENT position-tracking-enabling connector 55.

In an embodiment, position sensor 60 sends position signals to a position tracking system. Without an enablement from ENT position-tracking-enabling connector 55 position sensor 60 will not be functional. In an embodiment, the position tracking system comprises a magnetic position tracking system, such as CARTO™ position tracking that is part of system 20. The CARTO™ position tracking system is configured to track the position of one or more position sensors in the head of patient 22.

System 20 comprises a location pad 40, which comprises field-generators 44 fixed on a frame 46. Position sensor 60 generate position signals in response to the sensed external magnetic fields from the field generators, thereby enabling a processor 34 to map the position of sensor 60 in a coordinate system of system 20. Location pad 40 that defines a fixed coordinate system to which the position of sensor 60 is mapped. In the exemplary configuration shown in FIG. 1, pad 40 comprises five field-generators 44 but may comprise any other suitable number of generators 44. Pad 40 further comprises a pillow (not shown) placed under a head 41 of patient 22, such that generators 44 are located at fixed, known positions external to patient 22.

In some embodiments, system 20 comprises console 33, which comprises a processor 34, typically a general-purpose computer, with suitable front end and interface circuits for receiving signals from tool 28 having a magnetic type of position sensor 60 attached thereon, via a cable 32, and for controlling other components of system 20 described herein.

Console 33 further comprises input devices 39 and a user display 36, which is configured to display relevant data (e.g., position coordinates) received from processor 34 or inputs inserted by physician 24. Console 33 comprises a driver circuit (not shown), which is configured to drive field-generators 44 with suitable signals so as to generate magnetic fields in a predefined working volume around head 41.

This method of position sensing using magnetic fields is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Position-Tracking-Enabling Connector for an ENT Tool

Figure 2:
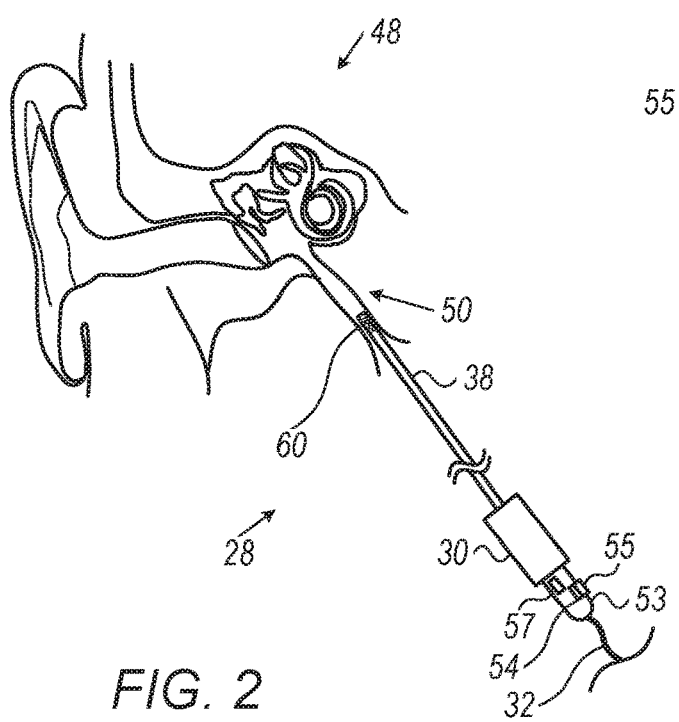
FIG. 2 is a sectional side view of an ear, and an ENT invasive instrument with a position-tracking-enabling connector plugged into a receptacle at its handle, in accordance with an embodiment of the present invention.

FIG. 2 is a sectional side view of an ear 48 and an ENT invasive instrument, such as insertion tube 28, with ENT position-tracking-enabling connector 55 plugged into a receptacle 54 at its handle 53, in accordance with an embodiment of the present invention.

During the medical procedure, physician 24 operates insertion tube 28 so as to insert ENT tool 38 into the patient's ENT system, in the present example into Eustachian tube 50. ENT tool 38 is coupled to ENT apparatus 30, located externally to patient 22 and may be used by physician 24 for navigating ENT tool 38 from the nose to Eustachian tube 50 of ear 48. Additionally or alternatively, any other suitable apparatus may be used by the physician for the navigation of ENT tool 38.

In some embodiments, ENT tool 38 further comprises a position sensor 60 connected to a position tracking system, as described in FIG. 1 above. ENT apparatus 30 is equipped with receptacle 54 in its handle 53. ENT position-tracking-enabling connector 55 can plug into receptacle 54, to enable position sensor 60 to track the position of ENT tool 38 in Eustachian tube 50.

In some embodiments, while position-tracking-enabling connector 55 is not plugged into receptacle 54, sensor 60 is electrically disconnected or disabled in a secured manner. For example, in an embodiment interrogation circuitry 57 inside handle 53 is wired to receptacle 54, and comprises passive circuitry (e.g. soldered interconnects) that may or may not become connected by enablement circuitry located inside position-tracking-enabling connector 55 (Seen in FIG. 3). The decision is taken by the enablement circuitry, depending on terms of use encoded into position-tracking-enabling connector 55.

In the disclosed example, thus, when ENT position-tracking-enabling connector 55 is plugged into receptacle 54, and the terms of use encoded into position-tracking-enabling connector 55 are valid, the enablement circuitry in connector 55 closes a circuit in series with interrogation circuitry 57, causing position sensor 60 to become available to a control console (such as one shown in FIG. 1), and by doing so enables position tracking.

The configurations of ENT insertion tube 28, and particularly of ENT position-tracking-enabling connector 55, described in FIGS. 1 and 2, are depicted purely by way of example. In alternative embodiments, ENT position-tracking-enabling connector 55 may comprise any suitable configuration, having any suitable size and shape and arranged so that, for example, it may enable positioning functionality for more than one ENT tool, for example, for an ablation catheter and for a suction tool. Instead of receptacle 54, any type, shape and form of connecter may be used, for example a plug that fits a receptacle included in ENT position-tracking-enabling connector 55. As another example, position sensor 60, which in the embodiment described in FIGS. 1 and 2 is a magnetic sensor, may comprise a single coil or any other suitable number of coils configured to generate position signals.

Figure 3:
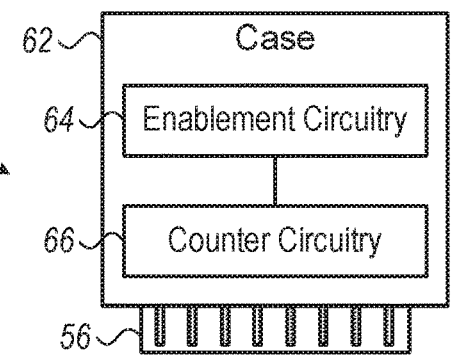
FIG. 3 is a block diagram that schematically illustrates a position-tracking-enabling connector, in accordance with an embodiment of the present invention.

FIG. 3 is a block diagram that schematically illustrates ENT position-tracking-enabling connector 55, in accordance with an embodiment of the present invention. As seen from the outside, position-tracking-enabling connector 55 comprises a case 62 and a plug 56. Inside case 62, position-tracking-enabling connector 55 comprises enablement circuitry 64 and counter circuitry 66.

In some embodiments, ENT position-tracking-enabling connector 55 enables the operation of position sensor 60 only under terms of use encoded therein, e.g., given usage-sessions and/or an expiration date, as explained below. In the example of FIG. 3, enablement circuitry 64 and/or counter circuitry 66 are configured to hold encoded terms of use and correspondingly to selectively enable position sensor 60 to send position signals to console 33. In the case where the encoded terms of use comprise a given maximal number of usage-sessions, counter circuitry 66 is configured to indicate to enablement circuitry 64 whether the preset maximal number of usage-sessions has been reached, and enablement circuitry 64 is configured to disable (i.e., deactivate) the position sensor communication when the usage-sessions reached a preset maximal number.

In an embodiment, position-tracking-enabling connector 55 includes a Radio-Frequency Identification (RFID) circuit. Once position-tracking-enabling connector 55 is plugged into ENT insertion tube 28, encoded terms of use are validated using the RFID circuit, and if the encoded terms of use are valid, position-tracking-enabling connector 55 enables position sensor 60 to send position signals to console 33.

Figure 4A:
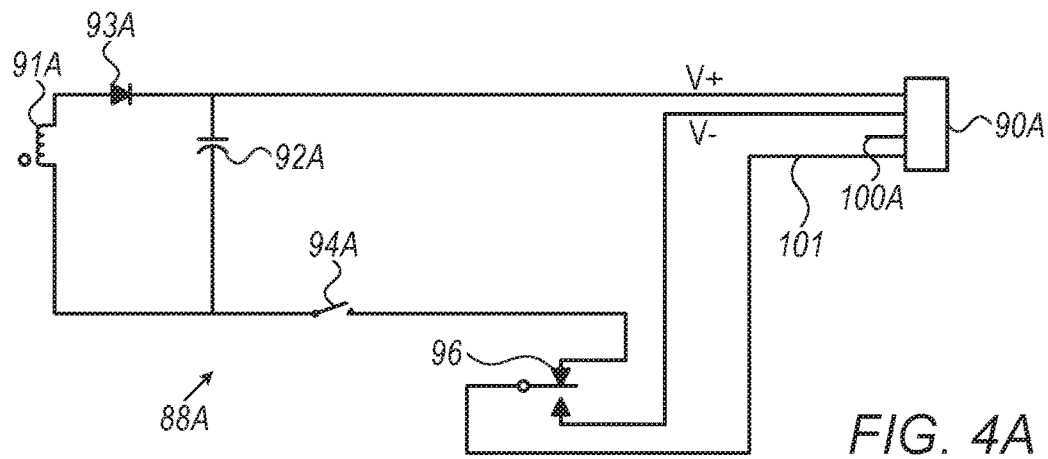
FIGS. 4A and 4B are circuit diagrams showing principles of operation of counter circuits, in accordance with embodiments of the present invention.
Figure 4B:
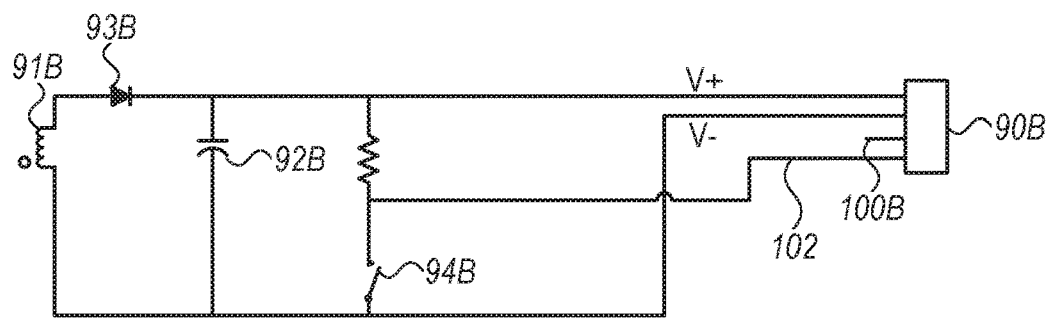

FIGS. 4A and 4B are detailed circuit diagrams showing principles of operation of counter circuits 88A and 88B, respectively, in accordance with embodiments of the present invention.

In an embodiment, circuit 88A shown in FIG. 4A, which is included in counter circuitry 66, comprises a usage-sessions counter 90A, which is configured to count sessions of usage of the ENT medical instrument. An induction coil 91A charges a capacitor 92A when ENT tool 38 (and thus sensor 60) is exposed to the magnetic field generated by field-generators 44. A diode 93A ensures the electrical current is direct current (DC). When ENT position-tracking-enabling connector 55 is plugged into connector 54, connector 54 shorts (closes) switch 94A in circuit 88A. Voltage supply is then provided to counter 90A that includes a small nonvolatile memory.

Whenever ENT connector 55 is plugged into connector 54 the counter 90A receives voltage supply and increments the count of usage sessions by one, from the last value stored at its memory. Counter 90A then self-disconnects itself by switching a relay 96 as commanded by counter 90A via line 101. In an optional embodiment, the number of previously-held usage-sessions and/or of the remaining number of usage-sessions is read from pin 100A of counter 90A, for example to be displayed to the physician on an alphanumeric display.

In another embodiment, circuit 88B shown in FIG. 4B, which is included in counter circuitry 66, comprises a coil 91B, a capacitor 92B, a diode 93B and a switch 94B having similar functions to coil 91A, capacitor 92A, diode 93A and switch 94A of circuit 88A. Counter 90B, however, is configured to count instants of usage by dates (e.g., count individual usage days). For this purpose, circuitry 88B receives a constant power supply so it is always on. Circuit 88B logs the date of plugging and/or unplugging ENT position-tracking-enabling connector 55 to/from connector 54. Therefore, if, for example, the physician disconnects and connects ENT position-tracking-enabling connector 55 multiple times on the same day, these multiple sessions will not increase the number of usage sessions counted, for example the number of days already used.

In an embodiment, Counter 90B logs the plugging and/or unplugging of ENT position-tracking-enabling connector 55 by line 102 receiving voltage, or stopping to receive voltage, respectively, each time switch 94B is closed or opened (i.e., by respectively plugging or unplugging ENT position-tracking-enabling connector 55). In an optional embodiment, the count of past usage days and/or of remaining usage days is read from a pin 100B of counter 90B, for example to be displayed to the physician on an alphanumeric display.

In an embodiment, identification circuitry 64 and counter circuitry 66 are both integrated on a single printed circuit board. The various elements of position-tracking-enabling connector 55 may be implemented in hardware, e.g., using one or more discrete components, Field-Programmable Gate Arrays (FPGAs) or Application-Specific Integrated Circuits (ASICs). In some embodiments, some elements of position-tracking-enabling connector 55, e.g., counter circuitry 66, may be implemented in software, or using a combination of software and hardware elements. The configuration of position-tracking-enabling connector 55 shown in FIG. 3 is an example configuration, which is depicted purely for the sake of conceptual clarity. In alternative embodiments, position-tracking-enabling connector 55 may be implemented using any other suitable components or configuration.

Figure 5:
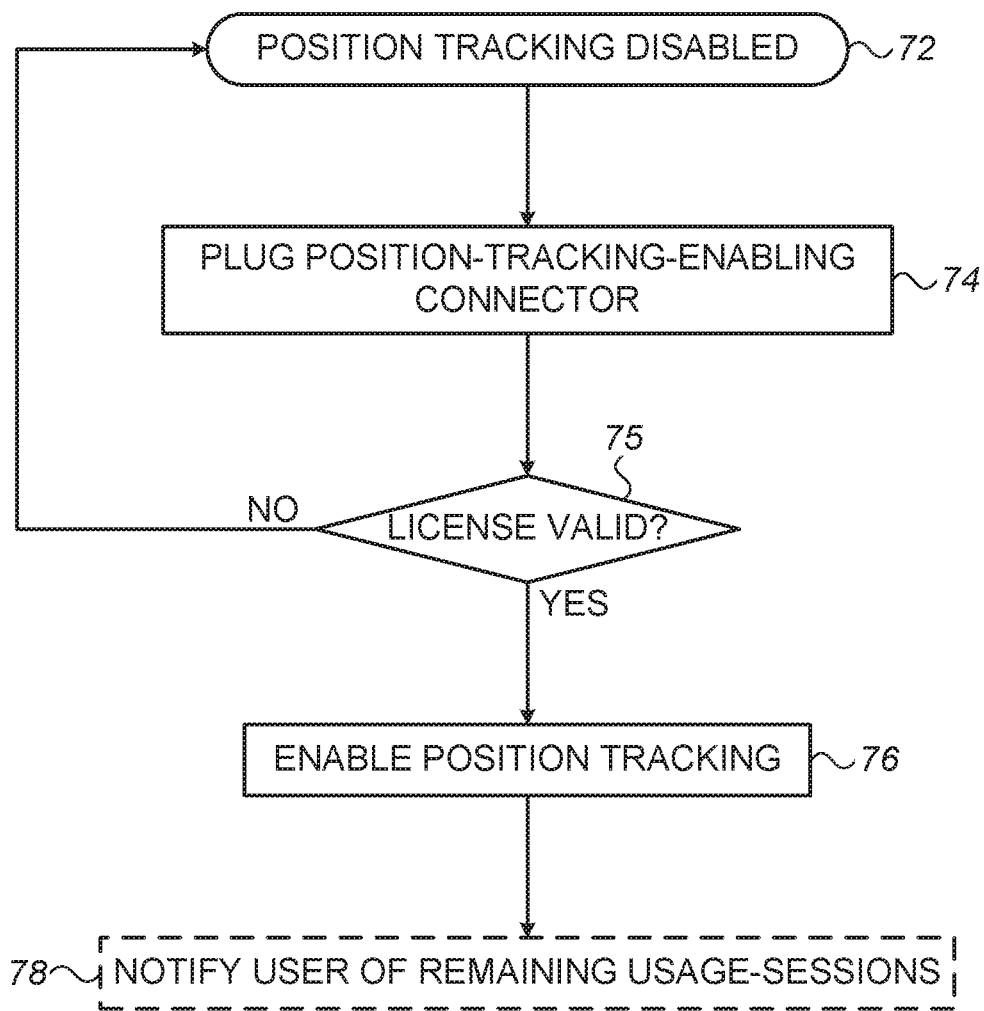
FIG. 5 is a flow chart that schematically illustrates a method for enabling and controlling the operation of a position sensor using a position-tracking-enabling connector, in accordance with an embodiment of the present invention.

FIG. 5 is a flow chart that schematically illustrates a method for enabling and controlling the operation of a position sensor using ENT position-tracking-enabling connector 55, in accordance with an embodiment of the present invention. As seen, the position tracking functionality (e.g. given by position sensor 60) is initially disabled, at a disablement step 72. At this stage, in the example disclosed in FIGS. 1 and 2, interrogation-circuitry 57 in handle 53 of ENT invasive instrument 28 did not yet become interconnected via enablement circuitry 64 in position-tracking-enabling connector 55. At an activation step 74 physician 24 plugs position-tracking-enabling connector 55 into receptacle 54. Interrogation-circuitry 57 then becomes interconnected via enablement circuitry 64 (i.e., the medical instrument 'detects' the presence of position-tracking-enabling connector 55).

At a checking step 75, enablement circuitry 64 checks whether the terms of use encoded into one of position-tracking-enabling connector 55 circuits (such as number of remaining usage-sessions (i.e., if a maximal number of usage-sessions value has been reached), as counted by counter circuitry 66) are valid. If so, enablement circuitry 64 enables position sensor 60 operation, at an enablement step 76. Otherwise, i.e., if enablement circuitry 64 detects that terms of use encoded into position-tracking-enabling connector 55 are invalid, enablement circuitry 64 maintains position sensor 60 disabled, looping back to disablement step 72.

In an optional embodiment, an alpha-numeric display contained in case 62 of position-tracking-enabling connector 55 presents to physician 24 the remaining usage-sessions, for example by receiving the remaining usage-sessions from counter 90A, at a notification step 78.

The example configurations of ENT invasive instrument 28 and position-tracking-enabling connector 55 shown in the figures are chosen purely for the sake of conceptual clarity.

In alternative embodiments, the disclosed techniques may be implemented using other suitable configurations comprising, for example, other ENT tools and ENT systems, such as an ablation catheter connected to a position tracking and ablation system. The architecture and functionality of the position-tracking-enabling connector may vary, such as for example its circuitry and the details of the encoded terms of use with the coupled medical instrument, and how these terms are encoded. In an alternative embodiment, invasive instrument 28 may include both an active interrogation-circuitry, and active enablement circuitry. ENT position-tracking-enabling connector 55 may comprise then passive encoded circuitry. In an optional embodiment an Electronically Erasable Programmable Read-Only Memory (EEPROM) and/or Flash memory, may be fitted into various circuits of ENT position-tracking-enabling connector 55 as to perform at least part of its functionalities, such as the interrogation and the enablement.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for using a medical instrument that comprises a shaft for insertion into a body of a patient, one or more position sensors fitted at a distal end of the shaft, and a connector, the method comprising:
   (a) placing the medical instrument into a connected state in which a mating connector is connected to the connector and the medical instrument is coupled to a processor; and
   (b) placing the medical instrument into a disconnected state in which the mating connector is disconnected from the connector and the medical instrument is coupled to the processor, wherein the act of placing the medical instrument into the disconnected state results in the one or more position sensors being communicatively isolated from the processor.

2. The method according to claim 1, wherein the medical instrument is configured for use with Ear-Nose-Throat (ENT) clinical applications.

3. The method according to claim 1, further comprising when the medical instrument is in the connected state, placing the one or more position sensors in operative communication with the processor and tracking a position of the distal end in the body using the one or more position sensors.

4. The method according to claim 3, wherein tracking the position of the distal end comprises sending position signals from the one or more position sensors to the processor.

5. The method according to claim 3, further comprising:
   (a) validating position-tracking terms-of-use, wherein the act of placing the one or more position sensors in operative communication with the processor is performed in response to the terms-of-use being valid; and (b) communicatively isolating the one or more position sensors from the processor when the mating connector is connected to the connector in response to the terms-of-use being invalid.

6. The method according to claim 5, further comprising counting a number of usage-sessions of the medical instrument, wherein the act of validating includes comparing the counted number to a predetermined maximal number of usage-sessions.

7. The method according to claim 6, wherein the terms-of-use are valid when the counted number is less than the predetermined maximal number, wherein the terms-of-use are invalid when the counted number is equal to the predetermined maximal number.

8. The method according to claim 5, wherein the act of validating is performed using a Radio-Frequency Identification (RFID) circuit.

9. A medical instrument, comprising:
(a) a shaft having a distal end, wherein the shaft is configured to be inserted into a body of a patient;
(b) at least one position sensor, wherein the at least one position sensor is located at the distal end of the shaft;
(c) a first connector;
(d) a proximal cable;
(e) a second connector, wherein the second connector is configured to connect with the first connector, wherein the second connector comprises circuitry configured to dictate whether to place the proximal cable into operative communication with the at least one position sensor or to communicatively isolate the proximal cable from the at least one position sensor, wherein the second connector is configured to place the proximal cable into operative communication with the at least one position sensor in response to the second connector being connected with the first connector and the circuitry dictating to place the proximal cable into operative communication with the at least one position sensor, wherein the second connector is configured to communicatively isolate the proximal cable from the at least one position sensor in response to the second connector being connected with the first connector and the circuitry dictating to communicatively isolate the proximal cable from the at least one position sensor, wherein disconnection of the second connector from the first connector results in the proximal cable being communicatively isolated from the at least one position sensor; and
(f) a processor, wherein the proximal cable is in operative communication with the processor when the second connector is connected with the first connector, wherein the proximal cable is in operative communication with the processor when the second connector is disconnected from the first connector.

10. The medical instrument according to claim 9, wherein the second connector is configured to place the proximal cable in operative communication with the at least one position sensor in response to terms of use provided on the second connector being valid when the second connector is connected with the first connector to enable tracking the position of the distal end, wherein the second connector is configured to communicatively isolate the proximal cable from the at least one position sensor in response to the terms of use provided on the second connector being invalid when the second connector is connected with the first connector.

* * * * *